(12) United States Patent
Lee

(10) Patent No.: US 9,510,818 B2
(45) Date of Patent: Dec. 6, 2016

(54) TWIST-GRIP ANCHORS AND METHODS OF USE

(71) Applicant: St. Jude Medical Luxembourg Holdings SMI S.A.R.L. ("SJM LUX SMI"), Plano, TX (US)

(72) Inventor: Jeffrey J. Lee, San Ramon, CA (US)

(73) Assignee: St. Jude Medical Luxembourg Holdings SMI S.A.R.L. ("SJM LUX SMI"), Luxembourg (LU)

( * ) Notice: Subject to any disclaimer, the term of this patent is extended or adjusted under 35 U.S.C. 154(b) by 0 days.

(21) Appl. No.: 13/827,686

(22) Filed: Mar. 14, 2013

(65) Prior Publication Data

US 2014/0155936 A1    Jun. 5, 2014

Related U.S. Application Data

(60) Provisional application No. 61/733,813, filed on Dec. 5, 2012.

(51) Int. Cl.
*A61B 17/04*    (2006.01)
*A61N 1/05*    (2006.01)

(52) U.S. Cl.
CPC ......... *A61B 17/0401* (2013.01); *A61N 1/0558* (2013.01); *A61N 2001/0582* (2013.01)

(58) Field of Classification Search
CPC   A61M 5/1418; A61M 5/16813; A61M 25/02; A61M 2025/024; A61N 1/0558; A61N 2001/0582; A61B 17/0401
USPC .......... 604/174, 175, 178, 248, 250
See application file for complete search history.

(56) References Cited

U.S. PATENT DOCUMENTS

| | | | |
|---|---|---|---|
| 5,476,493 A * | 12/1995 | Muff | 607/119 |
| 5,957,968 A | 9/1999 | Belden et al. | |
| 7,398,125 B2 * | 7/2008 | Osypka et al. | 607/119 |
| 7,930,039 B2 * | 4/2011 | Olson | 607/126 |
| 8,002,749 B2 * | 8/2011 | Macatangay et al. | 604/167.03 |
| 8,249,719 B2 | 8/2012 | Bodner et al. | |
| 8,311,643 B2 | 11/2012 | North | |
| 2010/0179562 A1 | 7/2010 | Linker et al. | |
| 2010/0274336 A1 | 10/2010 | Nguyen-stella et al. | |

OTHER PUBLICATIONS

International search report and written opinion dated Mar. 3, 2014 for PCT Application No. US2013/073407.

* cited by examiner

*Primary Examiner* — Theodore Stigell

(57) ABSTRACT

Devices, systems and methods are provided for anchoring implantable medical devices to maintain an implanted position. In particular, twist-grip anchors are provided. In some embodiments, the twist-grip anchor comprises a first support having a first lumen, a second support having a second lumen, and a sleeve having a first end fixedly attached to the first support and a second end fixedly attached to the second support, wherein the first and second supports and the sleeve are aligned to allow the passage of the elongate device through the first lumen, second lumen and sleeve, and wherein rotation of at least the first support twists the sleeve so that the sleeve engages the elongate device in a manner that resists movement of the elongate device in relation to the sleeve. The anchor is then attached to the tissue, such as by suturing.

26 Claims, 3 Drawing Sheets

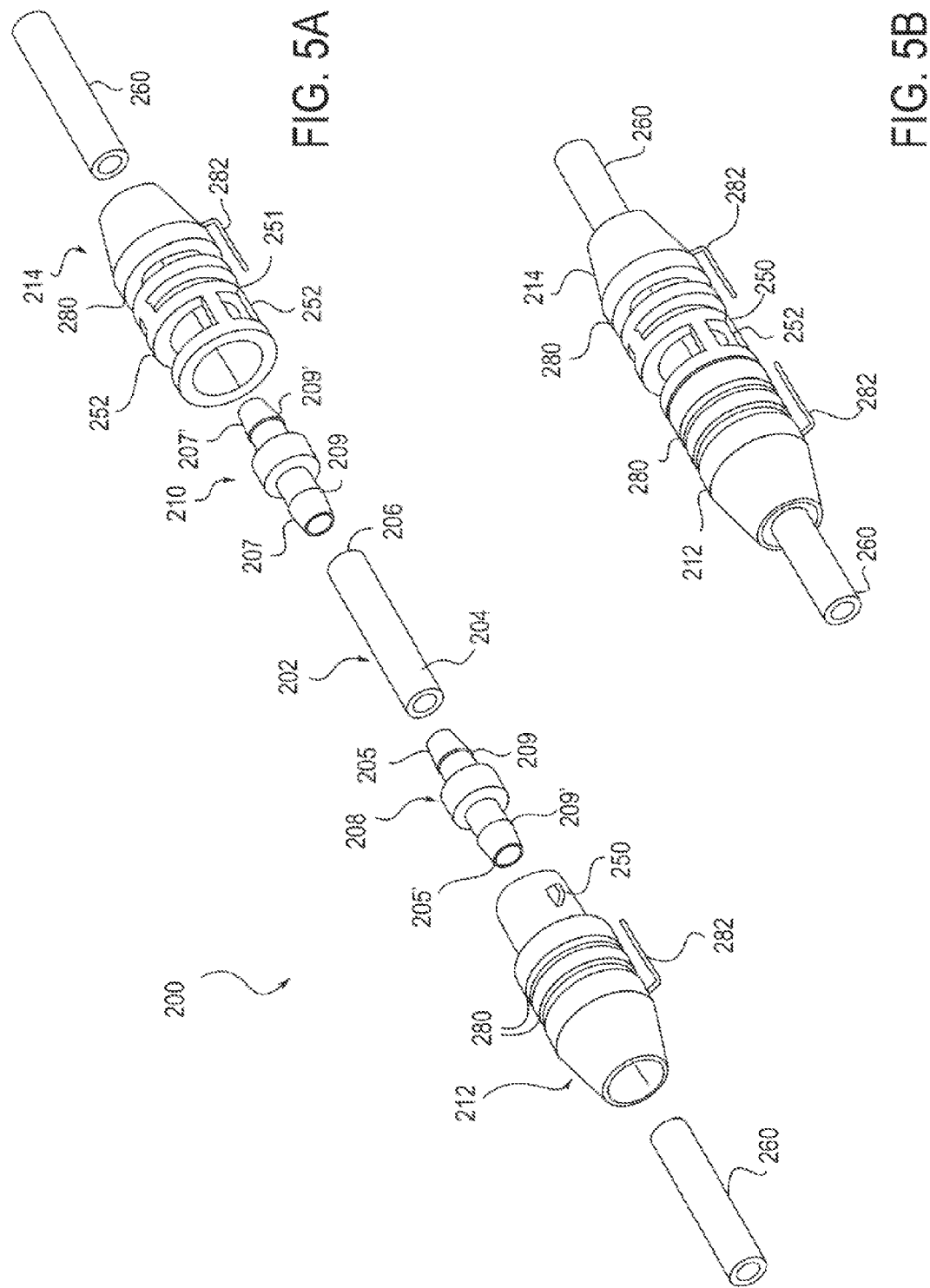

TWIST-GRIP ANCHORS AND METHODS OF USE

CROSS-REFERENCES TO RELATED APPLICATIONS

This application claims priority under 35 U.S.C. 119(e) to U.S. Provisional Patent Application No. 61/733,813, entitled "Twist-Grip Anchors and Methods of Use", filed on Dec. 5, 2012, which is incorporated herein by reference.

STATEMENT AS TO RIGHTS TO INVENTIONS MADE UNDER FEDERALLY SPONSORED RESEARCH AND DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

Electrical stimulation and drug delivery to portions of the anatomy, particularly the spinal anatomy and peripheral nervous system, often involve the implantation of one or more leads or delivery devices within the patient's body. The leads or delivery devices extend between the target anatomy and an implantable pulse generator (IPG) or drug reservoir which is typically implanted at a remote location. Precise positioning of the leads or delivery devices is desired to optimize treatment. Accuracy in administration of the drugs or stimulation to a particular target location can maximize beneficial effects of treatment and patient satisfaction. It is desired that such accuracy be maintained over time to ensure continued successful treatment.

For example, when implanting an epidural lead, a physician must surgically open the body tissue to the epidural space, and then insert the lead into the epidural space to the desired location. Fluoroscopy aids the physician, and trial and error tests of treatment define the desired location(s) for treatment. Once desirably positioned, it is desired to maintain the lead in place. Typically this is attempted by suturing the lead in place, such as by attaching a sleeve or anchor to the lead and suturing the anchor to the lead and to the surrounding tissue where the lead enters the epidural space. A variety of conventional anchors are available for such use. Some conventional anchors are comprised of silicone and are attached to the lead with sutures. However, such anchors often do not sufficiently grip the lead and the lead grip force is highly dependent on the suturing technique of the physician. Such suturing is time consuming, tedious and subject to error or variability. Further, any repositioning of the anchor along the lead requires removal of the sutures and resuturing. Other conventional anchors are attached to the lead with a mechanically actuated mechanism. Although such anchors are sometimes more effective in gripping the lead, the anchors can potentially damage the lead or cause severe deformation of the lead body. In addition, the mechanically actuated anchors are most suited for leads with relatively rigid bodies and are not suitable for leads having more flexible bodies.

It is desired to provide mechanisms for anchoring leads, catheters or other devices within body tissue that are easy and efficient to use, reliable, and adjustable. At least some of these objectives will be met by the present invention.

SUMMARY OF THE INVENTION

Aspects of the present disclosure provide devices, systems, and methods for anchoring implantable medical devices to maintain an implanted position.

In a first aspect of the present invention, an anchor is provided for anchoring an elongate device to tissue within a patient. In some embodiments, the anchor comprises a first support having a first lumen, a second support having a second lumen, and a sleeve having a first end fixedly attached to the first support and a second end fixedly attached to the second support, wherein the first and second supports and the sleeve are aligned to allow the passage of the elongate device through the first lumen, second lumen and sleeve, and wherein rotation of at least the first support twists the sleeve so that the sleeve engages the elongate device in a manner that resists movement of the elongate device in relation to the sleeve, and wherein the anchor is configured for attachment to the tissue.

In some embodiments, the sleeve is compliant and conforms to the elongate device in an atraumatic manner during engagement. In such embodiments, the sleeve is typically comprised of silicone, polyurethane, or silicone-urethane copolymers.

In some embodiments, level of engagement is adjustable by increasing or decreasing the amount of twist. In some embodiments, engagement atraumatically deforms the elongate device in a manner that assists in resistance of movement of the elongate device in relation to the sleeve.

It may be appreciated that in some embodiments, rotation offsets the first and second supports by 90-180 degrees. Optionally, rotation is in increments of 10 degrees. In some embodiments, the first and second supports are biased to rotate causing twisting of the sleeve in a relaxed state.

In some embodiments, the anchor further comprises a locking mechanism to lock the first and second supports in relation to each other. In some embodiments, the anchor further comprises an outer housing comprising a first piece fixedly attached to the first support and a second piece fixedly attached to the second support, wherein the first and second pieces rotate in relation to each other. In such embodiments, the first and second pieces may mate at a location over the sleeve.

In some embodiments, the anchor includes a groove for holding a suture which attaches the anchor to the tissue. Likewise, in some embodiments, the anchor includes a suture arm for supporting a suture which attaches the anchor to the tissue.

In some embodiments, the anchor further comprises a third support having a third lumen, and another sleeve having a first end fixedly attached to the second support and a second end fixedly attached to the third support, wherein the first, second and third supports and the sleeve are aligned to allow the passage of an elongate device through the first lumen, second lumen, third lumen and sleeve, and wherein rotation of at least one of the supports twists the sleeves so that the sleeves engage the elongate device in a manner that resists movement of the elongate device in relation to the sleeves.

In a second aspect of the present invention, a method is provided for anchoring an elongate device within a body of a patient. In some embodiments, the method comprises advancing an elongate device through a sleeve of an anchor, wherein the anchor comprises a first support, a second support, and the sleeve having a first end fixedly attached to the first support and a second end fixedly attached to the second support. The method further comprising rotating at least the first support in relation to the second support so as to twist the sleeve to engage the elongate device therein in a manner that resists movement of the elongate device in relation to the sleeve, and fixing the anchor to a tissue within the body.

In some embodiments, the method further comprises adjusting a level of engagement by increasing or decreasing the amount of twist.

In some embodiments, rotating offsets the first and second supports by 90-180 degrees. Optionally, rotating is in increments of 10 degrees.

In some embodiments, the rotating step is achieved by actuating the anchor, wherein the first and second supports are biased to rotate upon actuation causing twisting of the sleeve in a relaxed state.

In some embodiments, the elongate device exits an epidural space at an epidural access point, and wherein fixing the anchor comprises suturing the anchor to tissue near the epidural access point.

Other objects and advantages of the present invention will become apparent from the detailed description to follow, together with the accompanying drawings.

BRIEF DESCRIPTION OF THE DRAWINGS

FIGS. 5A-5B illustrate another embodiment of the twist-grip anchor.

DETAILED DESCRIPTION OF THE INVENTION

Figure 1:
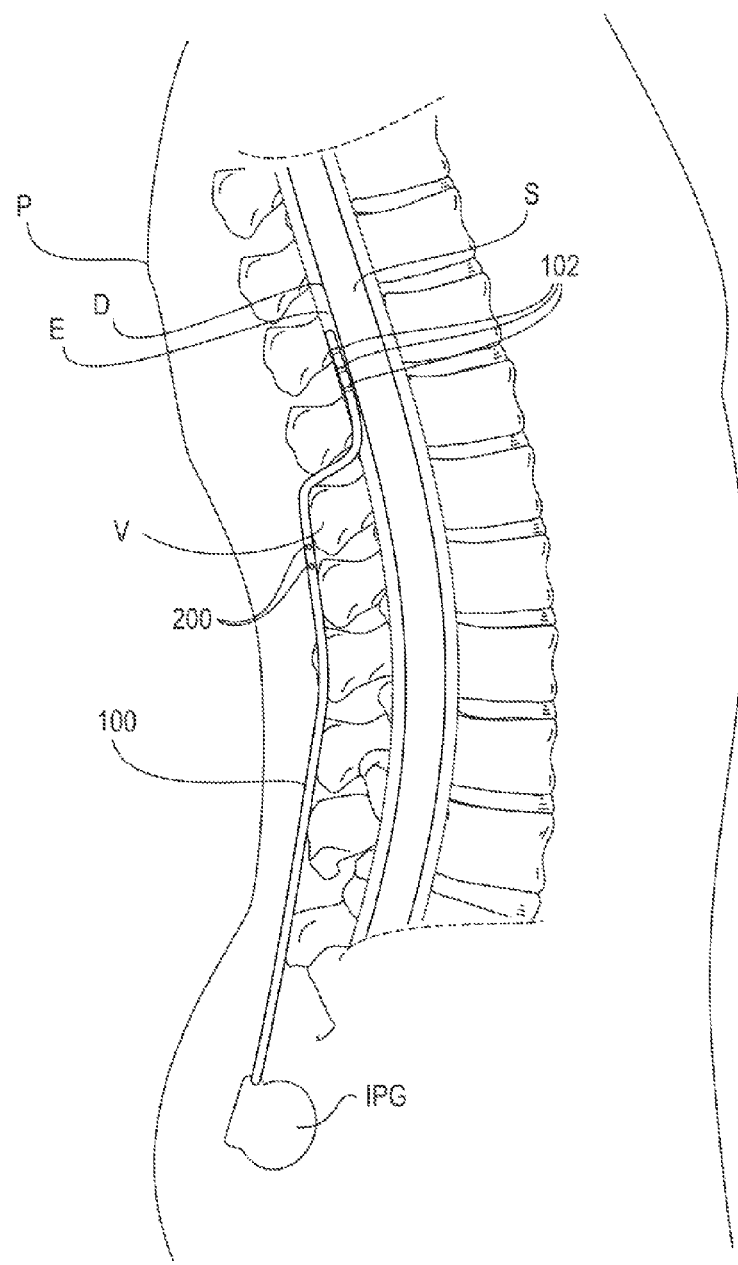
FIG. 1 illustrates an example of such an implantable lead advanced into the epidural space.

The present invention provides devices, systems and methods for anchoring implantable medical devices to maintain an implanted position. In some embodiments, the medical devices are stimulation leads which are implanted near a portion of the neural anatomy for providing stimulation thereto. In some embodiments, at least one lead is advanced into the epidural space to apply stimulation energy to the spinal cord itself or to anatomies accessible via the epidural space, such as the dorsal root, dorsal root ganglion or peripheral nerves. FIG. 1 illustrates an example of such an implantable lead 100 advanced into the epidural space E. Here, the lead 100 is shown inserted between the vertebrae V, advanced within the epidural space E and positioned so that electrodes 102 disposed along its distal end are positioned against the dura layer of the spinal cord S. It may be appreciated that the lead 100 may be advanced further, such as to position the electrodes 102 near other spinal anatomy, such as the dorsal root ganglion. In any case, the lead 100 is implanted either through the skin via an epidural needle or through an open procedure involving a cut-down to the desired anatomy. When accessing via an epidural needle, the needle is inserted to the ligamentum flavum LF and a loss of resistance to injection technique is used to identify the epidural space. In addition to the loss of resistance technique, real-time observation of the advancing needle may be achieved with a portable ultrasound scanner or with fluoroscopy. Once the needle has been successfully inserted into the epidural space E, the syringe can be removed. The lead 100 is then delivered through the needle. When positioning a lead in, on, about, near, adjacent or in proximity to a dorsal root or dorsal root ganglion, the lead may be delivered with the use of various delivery devices, such as described and illustrated in U.S. patent application Ser. No. 12/687,737, entitled "Stimulation Leads, Delivery Systems and Methods of Use", filed Jan. 14, 2010, and incorporated by reference for all purposes.

In any case, the leads 100 extend from the epidural space E to an implantable pulse generator IPG which is implanted at a remote location, such as in the buttocks. To maintain position of the lead 100, the lead 100 is anchored to tissue outside of the epidural space at a desired point of anchoring. Such anchoring is achieved with a twist-grip anchor 200 of the present invention which is advanced along the lead 100 to the desired point of anchoring and actuated to securely grip the lead. The actuated anchor 200 is then secured to the surrounding tissue, such as by suturing.

Figure 2:
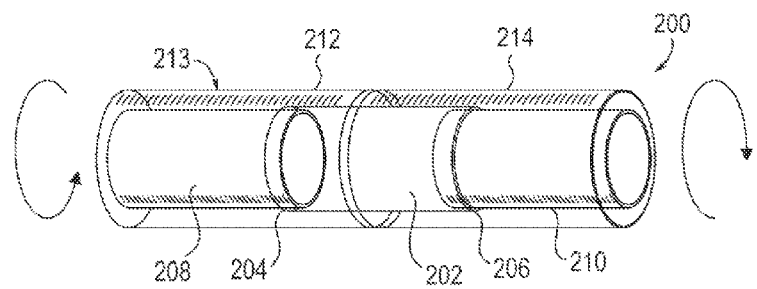
FIG. 2 illustrates an embodiment of the twist-grip anchor.

FIG. 2 illustrates an embodiment of the twist-grip anchor 200. In this embodiment, the anchor 200 is comprised of an inner sleeve 202 having a first end 204 and a second end 206. The inner sleeve 202 is comprised of an implantable flexible or semi-flexible material, such as silicone, polyurethane, silicone-urethane copolymers or other suitable materials. The first end 204 is fixedly attached to a first support 208 and the second end 206 is fixedly attached to a second support 210. The supports 208, 210 are comprised of a more rigid material which sufficiently maintains the inner diameter of the supports 208, 210 during actuation of the anchor 200. Example materials include polyetheretherketone, implantable acrylic, and stainless steel. The anchor 200 also includes a rotatable two-piece outer housing 213 comprised of a first piece 212 and a second piece 214. The first piece 212 is fixedly attached to the first support 208 and the second piece 214 is fixedly attached to the second support 210. In this embodiment, the first and second pieces 212, 214 extend over the inner sleeve 202 so that the inner sleeve 202 is encased by the housing 213. Typically, the first and second pieces 212, 214 mate at a location over the inner sleeve, such as in the center of the sleeve, as illustrated in FIG. 2. It may be appreciated, however, that the pieces 212, 214 may mate at other locations or may not mate at all. In some embodiments, the first and second pieces 212, 214 are circumferentially rotatable in opposite directions relative to each other around a central axis. In other embodiments, the first piece 212 is stationary and the second piece 214 rotates in relation to the first piece 212. Once rotated, the first and second pieces 212, 214 are offset from each other by, for example, up to 360 degrees, up to 270 degrees, up to 180 degrees, up to 90 degrees, up to 45 degrees, or less than 45 degrees. In preferred embodiments, the pieces 212, 214 are offset from each other by 90-180 degrees. In other embodiments, the pieces 212, 214 are rotatable in increments, such as in 10 degree increments. In any case, rotation offsets the first end 204 of the inner sleeve 202 relative to the second end 206 of the inner sleeve. This causes the inner sleeve 202 to twist and collapse. The outer housing 213 includes a locking mechanism which locks the first and second pieces 212, 214 together or in relation to each other. Thus, the first and second pieces 212, 214 can be rotated relative to each other and locked in the rotated position while maintaining the same axial length of the sleeve 202. This holds the sleeve 202 in the twisted position.

Figure 3:
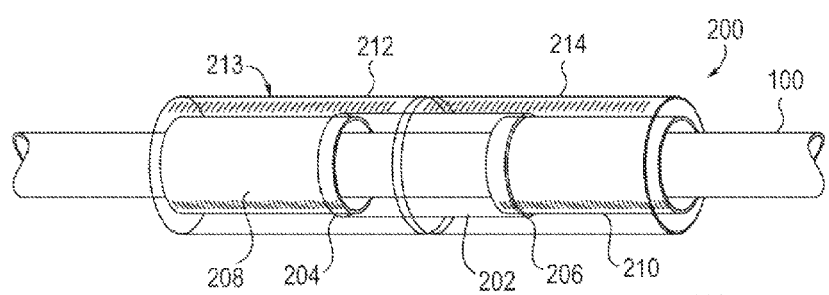
FIG. 3 illustrates the embodiment of the twist-grip anchor of FIG. 2 mounted on a lead 100.
Figure 4:
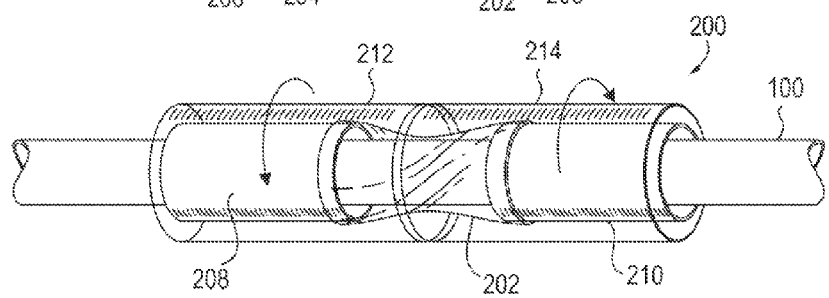
FIG. 4 illustrates the inner sleeve twisting and collapsing against the lead.

FIG. 3 illustrates the embodiment of the twist-grip anchor 200 of FIG. 2 mounted on a lead 100. The anchor 200 is advanceable along the lead 100 to a desired location for anchoring the lead 100 to surrounding tissue. Once desirably positioned, the anchor 200 is fixedly attached to the lead 100 by actuating the anchor 200. Actuation is achieved by rotating the first and/or second pieces 212, 214 relative to each other. This causes the inner sleeve 202 to twist and collapse against the lead 100, as illustrated in FIG. 4. Such collapse, along with the sleeve friction on the lead 100, retains the lead 100 axially and thus fixedly attaches the anchor 200 to the lead 100. Since the inner sleeve 202 is compliant, the sleeve 202 conforms to the lead 100 in an atraumatic manner which resists damage to the lead 100 and the anchor 200, even under conditions of motion fatigue. In some embodiments, twisting and collapse of the inner sleeve 202 causes slight deformation of the lead 100, particularly if the lead 100 is flexible. This assists in retaining the lead 100 and does so in a flexible manner, again resisting damage to the lead 100 and the anchor 200. Thus, the twist-grip anchor 200 is particularly suited for use with flexible leads which are typically difficult to retain without damage when using conventional anchors. The level of grip on the lead 100 can be adjusted by increasing or decreasing the amount of twist (i.e. by increasing or decreasing rotation of the first and/or second pieces 212, 214 relative to each other).

Once the desired level of grip is achieved, the pieces 212, 214 are locked in relation to each other to maintain the rotation. Such locking is achieved with a locking mechanism, such as a one-way ratchet with spring loading, a clutch arrangement, a cam and/or a plunger lock. In some embodiments, the locking mechanism is operated with the use of a tool, and in other embodiments the locking mechanism is operated by hand.

The anchor 200 can be disengaged or removed from the lead 100 by unlocking the locking mechanism and untwisting the inner sleeve 202. This is achieved by reversing the rotation of the relevant pieces 212, 214. The anchor 200 can then be repositioned and reengaged at a new desired location along the lead 100. However, in some embodiments, the locking mechanism is a one-time use wherein repositioning or removal of the anchor 200 involves clipping off or removing the locking mechanism. In such instances, if repositioning is desired, a new locking mechanism is attached to the anchor 200 or a new anchor having an intact locking mechanism is used.

FIGS. 5A-5B illustrate another embodiment of the twist-grip anchor 200. In this embodiment, the anchor 200 is comprised of an inner sleeve 202 having a first end 204 and a second end 206. Again, the inner sleeve 202 is comprised of an implantable flexible or semi-flexible material, such as silicone, polyurethane, silicone-urethane copolymers or other suitable materials. The first end 204 is attachable to a first support 208 and the second end 206 is attachable to a second support 210. In this embodiment, such attachment is achievable by fitting the sleeve ends 204, 206 over tapered bar fittings 205, 207 on the first and second supports 208, 210, respectively. Each bar fitting 205, 207 includes a sharp edge 209 which engages the sleeve, holding it in place. The sleeve ends 204, 206 are additionally held over the tapered bar fittings 205, 207 by friction. The supports 208, 210 are comprised of a more rigid material than the sleeve 202 which sufficiently maintains the inner diameter of the supports 208, 210 during actuation of the anchor 200. Example materials include polyetheretherketone, implantable acrylic, and stainless steel.

The anchor 200 also includes a rotatable two-piece outer housing comprised of a first piece 212 and a second piece 214. In this embodiment, the first piece 212 is attachable to the first support 208 and the second piece 214 is attachable to the second support 210. Each piece 212, 214 includes internal grooves to accept the corresponding protrusions on the supports 212, 214. In this embodiment, the first and second pieces 212, 214 extend over the inner sleeve 202 so that the inner sleeve 202 is encased by the housing, as illustrated in FIG. 5B. Typically, the first and second pieces 212, 214 mate at a location over the inner sleeve, such as in the center of the sleeve. It may be appreciated, however, that the pieces 212, 214 may mate at other locations or may not mate at all.

In some embodiments, the first and second pieces 212, 214 are circumferentially rotatable in opposite directions relative to each other around a central axis. In other embodiments, the first piece 212 is stationary and the second piece 214 rotates in relation to the first piece 212. Once rotated, the first and second pieces 212, 214 are offset from each other by, for example, up to 360 degrees, up to 270 degrees, up to 180 degrees, up to 90 degrees, up to 45 degrees, or less than 45 degrees. In preferred embodiments, the pieces 212, 214 are offset from each other by 90-180 degrees. In other embodiments, the pieces 212, 214 are rotatable in increments, such as in 10 degree increments. In any case, rotation offsets the first end 204 of the inner sleeve 202 relative to the second end 206 of the inner sleeve. This causes the inner sleeve 202 to twist and collapse.

The anchor 200 includes a locking mechanism which locks the first and second pieces 212, 214 in relation to each other. In this embodiment, the anchor 200 includes a locking button 250 disposed on the first piece 212 which engages a locking window 252 on the second piece 214. Thus, when the first and second pieces 212, 214 are mated together, the locking button 250 protrudes through a window 252, resisting disengagement of the pieces 212, 214 (i.e. locking the pieces 212, 214 together), as illustrated in FIG. 5B. In this embodiment, the first and second pieces 212, 214 can be rotated relative to each other and locked in the rotated position in the same motion. This holds the sleeve 202 in the twisted position. In this embodiment, unlocking or disengagement can be achieved by rotating the first and/or second pieces 212, 214 so that the button 250 is depressed by a crossbar 251 near the window 252. Once the button 250 is depressed, the first piece 212 can be disengaged from the second piece 214.

In this embodiment, the anchor 200 also includes strain relief sleeves 260. The strain relief sleeves 260 extend from each end of the anchor 200 to reduce strain on the portions of the elongate device entering and exiting the anchor 200. It may be typically desired that the elongate device or lead be soft and "floppy" so as to conform to bends in the anatomy along its path. In contrast, the external housing of the anchor may typically be a more rigid body configured to withstand encapsulation and tissue contraction. Thus, as the lead exits the anchor 200 the lead may endure an abrupt transition from fully supported by the anchor 200 to fully unsupported. This portion of the lead can be vulnerable to kinking, strain and damage. Thus, the strain relief sleeves 260 ease the transition by supporting the lead beyond the housing pieces 212, 214. Thus, the strain relief sleeves 260 are typically comprised of a material that is more flexible than the housing pieces 212, 214. In this embodiment, one sleeve 260 joinable with the first support 208 and another sleeve 260 is joinable with the second support 210. Such joining or attachment is achievable by fitting ends of the strain relief sleeves 260 over tapered bar fittings 205', 207' on the first and second supports 208, 210, respectively. Each bar fitting 205', 207' includes a sharp edge 209' which engages the strain relieve sleeve 260, holding it in place. The strain relief sleeve ends are additionally held over the tapered bar fittings 205', 207' by friction.

It may be appreciated that the twist-grip anchor 200 may be biased to twist and collapse against a lead 100 while in a relaxed state, wherein actuation opens the lumen of the inner sleeve 202 to allow advancement of the lead 100 therein. In such embodiments, the locking mechanism locks the first and second pieces 212, 214 together or in relation to each other in an unrotated, non-offset or aligned position. This allows the anchor 200 to be advanced along the lead 100. Once desirably placed, the locking mechanism may be disengaged or unlocked to allow the pieces 212, 214 to return to a biased rotation, twisting the inner sleeve 202 against the lead 100.

Figure 6:
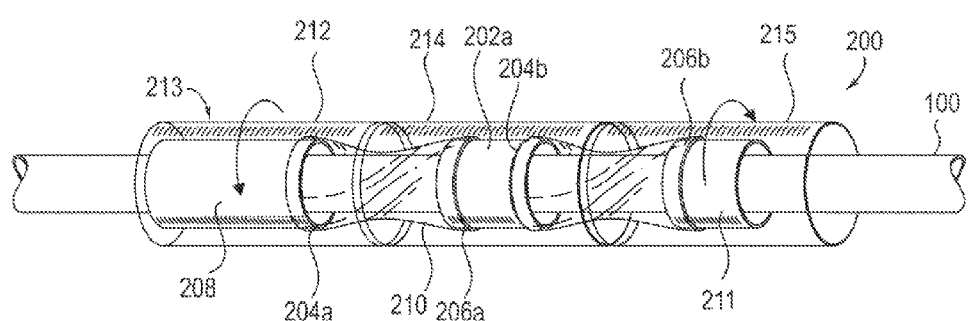
FIG. 6 illustrates an embodiment of an anchor having two inner sleeves.

It may be appreciated that in some embodiments, the anchor 200 includes more than one inner sleeve, such as illustrated in FIG. 6. The embodiment of FIG. 6 illustrates an anchor 200 having two inner sleeves 202a, 202b. Such inner sleeves 202a, 202b are axially aligned so that a lead 100 is passable through each of the sleeves 202a, 202b. In this embodiment, the first inner sleeve 202a has a first end 204a and a second end 206a and the second inner sleeve 202b has a first end 204b and a second end 206b. The anchor 200 includes three supports 208, 210, 211. The first end 204a of the first sleeve 202a is fixedly attached to the first support 208 and the second end 206a is fixedly attached to a second support 210. The first end 204b of the second sleeve 202b is fixedly attached to the second support 210 and the second end 204b is fixedly attached to the third support 211. The supports 208, 210, 211 are comprised of a more rigid material which sufficiently maintains the inner diameter of the supports 208, 210, 211 during actuation of the anchor 200.

In this embodiment, the anchor 200 also includes a rotatable three-piece outer housing 213 comprised of a first piece 212, a second piece 214, and a third piece 215. The first piece 212 is fixedly attached to the first support 208, the second piece 214 is fixedly attached to the second support 210, and the third piece 215 is fixedly attached to the third support 215. In this embodiment, the first and second pieces 212, 214 extend over the inner first inner sleeve 202a and mate at a location over the first inner sleeve, such as in the center of the sleeve. And, in this embodiment, the second and third pieces 214, 215 extend over the second inner sleeve 202b and mate and a location over the second inner sleeve, such as in the center of the sleeve. The first and second pieces 212, 214 are circumferentially rotatable in opposite directions relative to each other around a central axis. And, the second and third pieces 214, 215 are circumferentially rotatable in opposite directions relative to each other around the same central axis. In other embodiments, the second piece 214 is stationary while the first piece 212 and third piece 215 rotate in relation to the second piece 214. In other embodiments, the first and third pieces 212, 215 are stationary while the second piece 214 rotates in relation to the others. Rotation of some or all of the pieces 212, 214, 215 causes the inner sleeves 202a, 202b to twist and collapse against the lead 100. It may be appreciated that the pieces 212, 214, 215 may be independently rotatable or some or all of the pieces 212, 214, 215 may rotate together. The anchor 200 includes at least one locking mechanism which locks the pieces 212, 214, 215 in relation to each other.

It may also be appreciated that in some embodiments, the inner sleeve 202 is comprised of a rigid material. In such embodiments, the sleeve 202 is comprised of a tube having geometries, such as preferential cuts or cut-outs, which collapse around the lead 100 in a predetermined fashion when twisted. In some embodiments, the sleeve 202 includes cuts in a spiral arrangement which cause the sleeve 202 to collapse inward when rotated in one direction and extend outward when rotated in the opposite direction. Such collapse engages the sleeve with the lead and extension disengages the sleeve from the lead. In some embodiments, angled cuts around the circumference of the sleeve provide a similar benefit.

Typically, the anchor is sutureable to the surrounding tissue to hold the lead 100 in place in relation to the body. Such suturing typically involves wrapping the suture around the anchor 200 and suturing the anchor 200 to the tissue. In some embodiments, the anchor 200 includes indents or grooves 280 in the outer surface of the housing pieces 212, 214, such as illustrated in FIGS. 5A-5B. Such grooves 280 assist in maintaining position of the sutures and resist slippage of the anchor 200. In some embodiments, the anchor 200 additionally or alternatively has suture elements, such as suture arms 282, as illustrated in FIGS. 5A-5B. Suture arms 282 assist in suturing by providing an additional member to which a suture may be directly attached. Such suture arms 282 also provide an additional member which is grippable by the physician for manipulating the anchor. It may be appreciated that other suture elements include loops, handles, holes and protrusions, to name a few.

Although the anchor is typically sutured to the surrounding tissue to hold the lead 100 in place in relation to the body, it may be appreciated that the anchor 200 can alternatively or additionally be fixed in the body by positioning between tissue layers, so as to act as tissue-captured anchor in a manner described and illustrated in U.S. Provisional Patent Application No. 61/733,800, entitled "TISSUE-CAPTURED ANCHORS AND METHODS OF USE" filed on Dec. 5, 2012, and U.S. patent application Ser. No. 13/827,356, entitled "TISSUE-CAPTURED ANCHORS AND METHODS OF USE", which claims priority thereto, both incorporated herein by reference for all purposes. In such embodiments, the housing 213 may be altered to create a suitable shape (e.g. ball, disk, flange, etc), size and contour for anchoring between tissue layers. It may also be appreciated that in each of the above mentioned anchor designs, the anchor may be held in place by adhesive or suturing of the anchor to any of the surrounding tissue. It may also be appreciated that in each of the above mentioned anchor designs the housing 213 may have any suitable shape, such as a shape particularly suited for a particular placement within the anatomy. Example shapes include oblong, oval, cylindrical, round, disk, jelly bean, dog bone, bent, curved, etc.

It may also be appreciated that each of the above mentioned anchor designs may be comprised partially or wholly of a material which allows or encourages tissue ingrowth. Examples of such materials include a fabric, netting or screen. Alternatively or in addition, the anchor may include a surface geometry or texture which allows or encourages tissue ingrowth. In any case, such tissue ingrowth may assist in stabilizing the anchor and maintaining position of the anchor within the patient's body.

It may be appreciated that the anchor 200 may be used to anchor a variety of devices. Although the above anchor embodiments are described to be attached to leads, such anchors may be attached to any suitable device that is at least partially implantable. Examples of such devices include catheters, scopes, and lead wires, to name a few.

What is claimed is:

1. An anchor for anchoring an elongate device to tissue within a patient comprising:
    a first support having a first lumen;
    a second support having a second lumen;
    a sleeve having a first end fixedly attached to the first support, a second end fixedly attached to the second support, and an axial length,
    wherein the first and second supports and the sleeve are alignable to allow the passage of the elongate device through the first lumen, second lumen and sleeve having the axial length, and wherein manual rotation of at least the first support twists the sleeve while maintaining the same axial length of the sleeve so that the sleeve engages the elongate device in a manner that resists movement of the elongate device in relation to the sleeve, and wherein the anchor is configured for attachment to the tissue; and
    a locking mechanism to lock the first and second supports in relation to each other.

2. An anchor as in claim 1, wherein the sleeve is compliant and conforms to the elongate device in an atraumatic manner during engagement.

3. An anchor as in claim 2, wherein the sleeve is comprised of silicone, polyurethane, or silicone-urethane copolymers.

4. An anchor as in claim 1, wherein level of engagement is adjustable by increasing or decreasing the amount of twist.

5. An anchor as in claim 1, wherein engagement atraumatically deforms the elongate device in a manner that assists in resistance of movement of the elongate device in relation to the sleeve.

6. An anchor as in claim 1, wherein rotation offsets the first and second supports by 90-180 degrees.

7. An anchor as in claim 1, wherein rotation is in increments of 10 degrees.

8. An anchor as in claim 1, further comprising an outer housing comprising a first piece fixedly attached to the first support and a second piece fixedly attached to the second support, wherein the first and second pieces rotate in relation to each other.

9. An anchor as in claim 8, wherein the first and second pieces mate at a location over the sleeve.

10. An anchor as in claim 1, wherein the anchor includes a groove for holding a suture which attaches the anchor to the tissue.

11. An anchor as in claim 1, wherein the anchor includes a suture arm for supporting a suture which attaches the anchor to the tissue.

12. An anchor as in claim 1, further comprising
    a third support having a third lumen; and
    another sleeve having a first end fixedly attached to the second support and a second end fixedly attached to the third support,
    wherein the first, second and third supports and the sleeve are aligned to allow the passage of an elongate device through the first lumen, second lumen, third lumen and sleeve, and wherein rotation of at least one of the supports twists the sleeves so that the sleeves engage the elongate device in a manner that resists movement of the elongate device in relation to the sleeves.

13. An anchor as in claim 1, wherein the locking mechanism comprises a one-way ratchet with spring loading, a clutch arrangement, a cam, and/or a plunger lock.

14. An anchor as in claim 1, wherein the locking mechanism comprises a locking button disposed on one of the supports which engages a window in the other of the supports.

15. An anchor as in claim 1, wherein the locking mechanism is one-time use.

16. An anchor as in claim 1, wherein the locking mechanism is unlockable by reverse rotating the first support.

17. A method for anchoring an elongate device within a body of a patient comprising:
    advancing an elongate device through a sleeve of an anchor, wherein the anchor comprises a first support, a second support, and the sleeve having a first end fixedly attached to the first support, a second end fixedly attached to the second support and an axial length;
    manually rotating at least the first support in relation to the second support while maintaining the same axial length of the sleeve so as to twist the sleeve to engage the elongate device therein in a manner that resists movement of the elongate device in relation to the sleeve; and
    fixing the anchor to a tissue within the body.

18. A method as in claim 17, further comprising adjusting a level of engagement by increasing or decreasing the amount of twist.

19. A method as in claim 17, wherein rotating offsets the first and second supports by 90-180 degrees.

20. A method as in claim 17, wherein rotating is in increments of 10 degrees.

21. A method as in claim 17, wherein the elongate device exits an epidural space at an epidural access point, and wherein fixing the anchor comprises suturing the anchor to tissue near the epidural access point.

22. A method as in claim 15, further comprising locking the first support in relation to the second support.

23. A method as in claim 22, wherein locking comprises actuating a one-way ratchet with spring loading, a clutch arrangement, a cam, and/or a plunger lock.

24. A method as in claim 17, wherein manually rotating at least the first support in relation to the second support simultaneously locks the supports in relation to each other.

25. A method as in claim 24, wherein manually rotating at least the first support in relation to the second support engages a locking button with a window.

26. A method as in claim 25, further comprising unlocking the supports from each other by depressing the locking button so that it disengages from the window.

* * * * *